Figure 1:
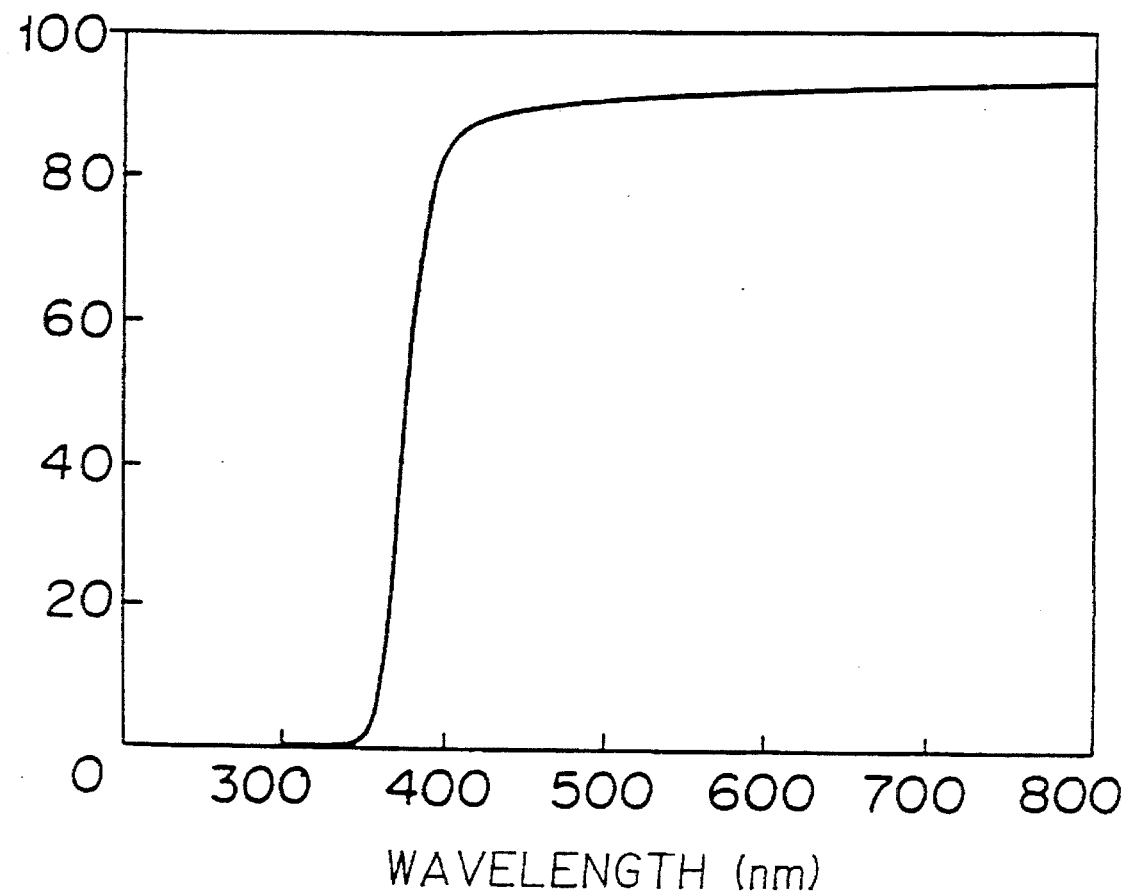

United States Patent [19]

Osawa et al.

[11] Patent Number: 5,468,904
[45] Date of Patent: Nov. 21, 1995

[54] FLUORINE-CONTAINING BENZOPHENONE DERIVATIVES AND USE THEREOF

[75] Inventors: Ryoko Osawa; Takashige Maekawa; Tatsuo Momii; Satoshi Kamata, all of Yokohama, Japan

[73] Assignee: Asahi Glass Company Ltd., Tokyo, Japan

[21] Appl. No.: 191,591

[22] Filed: Feb. 4, 1994

[30] Foreign Application Priority Data

| Feb. 9, 1993 | [JP] | Japan | 5-044564 |
| Jul. 28, 1993 | [JP] | Japan | 5-205874 |
| Dec. 28, 1993 | [JP] | Japan | 5-337237 |

[51] Int. Cl.$^6$ .................................................. C07C 49/786
[52] U.S. Cl. ........................... 568/333; 560/52; 560/150; 560/180; 560/182; 560/184; 560/228; 522/45
[58] Field of Search ........................ 568/333; 560/52, 560/150, 180, 182, 184, 228; 522/45

[56] References Cited

U.S. PATENT DOCUMENTS

| 2,976,259 | 3/1961 | Hardy et al. | 568/333 |
| 3,086,988 | 4/1963 | Gordon | 568/333 |
| 3,291,837 | 12/1966 | Goldberg et al. | 568/333 |
| 3,346,612 | 10/1967 | Hansen | 568/333 |
| 3,387,035 | 6/1968 | Gray et al. | |
| 3,387,635 | 6/1968 | Gray et al. | 568/333 |
| 5,030,701 | 7/1991 | Garbe | 526/245 |
| 5,202,359 | 4/1993 | McIntyre | 522/44 |
| 5,391,587 | 2/1995 | Wu | 522/45 |

FOREIGN PATENT DOCUMENTS

| 2084325 | 12/1971 | France . | |
| 2348181 | 11/1977 | France . | |
| 1768599 | 12/1971 | Germany | 568/333 |
| 2350180 | 4/1975 | Germany | 568/333 |
| 4114445 | 11/1991 | Germany . | |

*Primary Examiner*—James H. Reamer
*Attorney, Agent, or Firm*—Oblon, Spivak, McClelland, Maier, & Neustadt

[57] ABSTRACT

A fluorine-containing benzophenone derivative of the formula (1), (2) or (3):

$$\Phi^1(-X^1-Q^1-R_f^1)_n \quad (1)$$

$$\Phi^2-X^2-Q^2-R_f^2-Q^3-X^3-\Phi^3 \quad (2)$$

$$\Phi^4-X^4-Q_f-X^5-\Phi^5 \quad (3)$$

wherein $\Phi^1$ is a 2-hydroxybenzophenone structure of the formula ka-1:

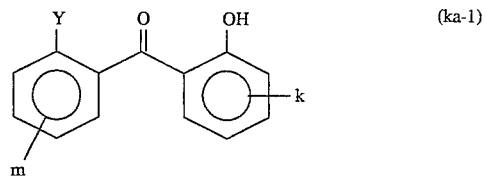

(wherein Y is a hydrogen atom or a hydroxyl group, each of k and m indicates the number of bond sites, k is an integer of from 0 to 3, and m is an integer of from 0 to 3, provided that $1 \leq (k+m) \leq 4$), n corresponds to (k+m) and is an integer of from 1 to 4, each of $\Phi^2$, $\Phi^3$, $\Phi^4$ and $\Phi^5$ is a 2-hydroxybenzophenone structure of the formula ka-1 wherein (k+m) is 1, each of $X^1$, $X^2$, $X^3$, $X^4$ and $X^5$ is a single bond or an oxygen atom, $Q^1$ is a single bond or a bivalent linking group having a carbon atom directly bonded to $X^1$, each of $Q^2$ and $Q^3$ is a single bond or a bivalent linking group, $R_f^1$ and $R_f^2$ are monovalent and bivalent polyfluorohydrocarbon group having from 2 to 22 carbon atoms, in which some of the carbon atoms may be substituted by ether oxygen atoms, and $Q_f$ is a bivalent linking group having at least one $Q^4-R_f^1$ (wherein $Q^4$ is a bivalent linking group).

10 Claims, 1 Drawing Sheet

FLUORINE-CONTAINING BENZOPHENONE DERIVATIVES AND USE THEREOF

The present invention relates to novel fluorine-containing benzophenone derivatives and their use as ultraviolet absorbers.

Polymer resin materials commonly used outdoors or indoors are exposed to various lights such as sunlight or lights of fluorescent lamps. Among them, lights of from 200 to 400 nm are ultraviolet rays hazardous to the resin materials and cause discoloration, color change or deterioration such as reduction of strength of the materials due to photo decomposition. Further, when such a resin material is used for coating a base material, even the base material to be protected will be adversely affected, since the resin coating does not have adequate ultraviolet absorptivity.

Heretofore, to protect a resin material or a base material coated with a resin material, it has been common to incorporate to the resin material an ultraviolet absorber such as benzophenone or benzotriazole, or various colorants depending upon the wavelengths of the lights to be absorbed. It is known that such compounds are capable of absorbing lights in the ultraviolet region and thus will be excited by ultraviolet rays, but the energy under excitation is converted within the molecules to a heat energy which is non-hazardous to the resin material, whereby deterioration of the resin material can be prevented.

Such an ultraviolet absorber is coated on the surface of the material or kneaded into the material itself at the time of molding the resin, to impart the ultraviolet absorptivity to the resin. When it is used as kneaded into a resin, however, there has been a problem such that its heat resistance at the molding temperature of the resin is poor, or when the resin is used in a severe environment for a long period of time, the compound tends to gradually bleedout of the resin. For the purpose of solving such a problem, it has been attempted to increase the vapor pressure of the ultraviolet absorber itself by introducing alkyl groups such as methyl groups, octyl groups or t-butyl groups to the structure of the ultraviolet absorber, or to make the ultraviolet absorber a polymer by introducing polymerizable moieties such as acryl groups, methacryl groups or vinyl groups thereto.

However, in view of the environment in which the resin material is practically used, or the heating temperature at the time of molding, it has still been desired to develop a high performance ultraviolet absorber which has higher heat resistance and lower bleedout tendency when incorporated into a molded product.

On the other hand, an attention has been drawn to a fluorine resin having excellent weather resistance and high transparency, as a protecting material for various base materials. A fluorine resin usually has high chemical resistance and weather resistance, but no substantial absorptivity of lights in the ultraviolet region of from 200 to 400 nm. Accordingly, when such a transparent fluorine resin is formed into a film and used as a surface protecting material for various base materials, there has been a problem that the coated substrates undergo deterioration due to ultraviolet rays passed through the coating. For the purpose of imparting absorptivity of ultraviolet rays to such a fluorine resin, an attempt has been made to incorporate a conventional ultraviolet absorber. However, the heat resistance of a usual ultraviolet absorber is too low at a usual molding temperature (at least about 200° C.) of a fluorine resin, and bleedout is also observed. Further, the compatibility with the fluorine resin is so low that a phenomenon of whitening is observed due to reduction of the transparency of the fluorine resin.

In order to prevent bleedout, an attempt has been made to increase the molecular weight of the ultraviolet absorber to a polymer level. However, the compatibility with the fluorine resin is still so low that the whitening phenomenon of the film is observed, and it is impossible to effectively shield only ultraviolet rays. Further, it has been attempted to use as an ultraviolet absorber a copolymer made of a monomer containing fluorine in its molecule and a monomer having ultraviolet absorptivity. However, it is still impossible to improve the compatibility with the fluorine resin.

Further, U.S. Pat. No. 3,387,035 discloses 2'-trifluoromethyl-2-hydroxy-4-methoxybenzophenones, and U.S. Pat. No. 3,346,612 discloses a 2-hydroxybenzophenone having a perfluorooctyl group via —OSO$_2$— at the 4-position. However, the former has drawbacks that the fluorine content is small, and the heat resistance and compatibility are poor, and the latter has a drawback that the weather resistance is poor.

It is an object of the present invention to provide an ultraviolet absorber which has high heat resistance and low bleedout tendency as compared with conventional ultraviolet absorbers and which can be incorporated not only to usual resins but also to fluorine resins and their molded products, to which it used to be difficult to impart ultraviolet absorptivity, particularly the one which can be incorporated to a fluorine resin having high transparency without impairing its light transmittance.

The present inventors have conducted detailed studies on the heat resistance, bleedout tendency, compatibility with usual resins and compatibility with fluorine resins having high transparency, of various conventional benzophenone type ultraviolet absorbing compounds. As a result, they have found that compounds having a polyfluorohydrocarbon group bonded to a benzophenone structure, have high heat resistance and show no substantial bleedout even when the resin has been molded at a high temperature, and further that they are capable of imparting ultraviolet absorptivity to fluorine resins to which it used to be difficult to incorporate ultraviolet-absorbing compounds, without impairing their transparency. Further, it has been found that a molded product of a resin having the compound of the present invention incorporated therein, has excellent weather resistance.

Thus, the present invention provides novel fluorine-containing benzophenone derivatives and their use.

Namely, the present invention provides a fluorine-containing benzophenone derivative of the formula (1), (2) or (3):

    (1)

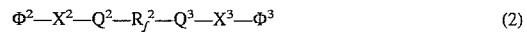    (2)

    (3)

wherein $\Phi^1$ is a 2-hydroxybenzophenone structure of the formula ka-3:

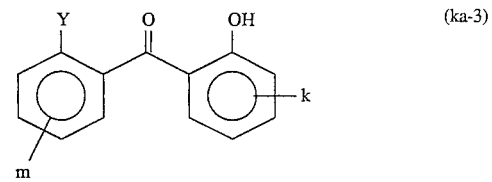    (ka-3)

(wherein Y is a hydrogen atom or a hydroxyl group, each of k and m indicates the number of bond sites, k is an integer of from 0 to 3, and m is an integer of from 0 to 3, provided that 1≦(k+m)≦4), n corresponds to (k+m) and is an integer of from 1 to 4, each of $\Phi^2$, $\Phi^3$, $\Phi^4$ and $\Phi^5$ is a 2-hydroxybenzophenone structure of the formula ka-3 wherein (k+m) is 1, each of $X^1$, $X^2$, $X^3$, $X^4$ $X^5$ is a single bond or a atom, $Q^1$ is a single bond or a bivalent linking group having a carbon atom directly bonded to $X^1$, each of $Q^2$ and $Q^3$ is a single bond or a bivalent linking group, $R_f^1$ is a monovalent polyfluorohydrocarbon group having from 2 to 22 carbon atoms, in which some of the carbon atoms may be substituted by ether oxygen atoms $R_f^2$ is a bivalent polyfluorohydrocarbon group having from 2 to 22 carbon atoms, in which some of the carbon atoms may be substituted by ether oxygen atoms, and $Q_f$ is a bivalent linking group having at least one $Q^4$—$R_f^1$ (wherein $Q^4$ is a bivalent linking group, and $R_f^1$ is as defined above).

In the accompanying drawing, FIG. 1 is a graph showing the light transmittance of the film of Example 19 plotted against the wavelength of light.

Now, the present invention will be described in detail with reference to the preferred embodiments.

In the formula (1), $\Phi^1$ is a 2-hydroxybenzophenone structure of the above formula ka-3. A hydroxyl group is bonded to a carbon atom at the 2-position of one of the two benzene rings of the 2-hydroxybenzophenone structure, and a hydroxyl group or a hydrogen atom, preferably a hydrogen atom, is bonded at the 2-position of the other benzene ring. Each of k and m in the formula ka-3 indicates the number of bond sites. Each of k and m is an integer of from 0 to 3, provided that $1 \leq (k+m) \leq 4$. Preferred is a case where (k+m) is 1.

n is the same as (k+m) and an integer of from 1 to 4.

Each of $\Phi^2$, $\Phi^3$, $\Phi^4$ and $\Phi^5$ in the formulas (2) and (3), is a 2-hydroxylbenzophenone structure of the formula ka-3 wherein (k+m) is 1. Y is a hydrogen atom or a hydroxyl group, preferably a hydrogen atom. $\Phi^2$ and $\Phi^3$, or $\Phi^4$ and $\Phi^5$, may be the same or different from each other, but they are preferably the same. Preferred is a 2-hydroxybenzophenone structure wherein k is 1 and m is 0.

Each of $\Phi^2$, $\Phi^3$, $\Phi^4$ and $\Phi^5$ is preferably a monovalent 2-hydroxybenzophenone structure of the formula ka-4:

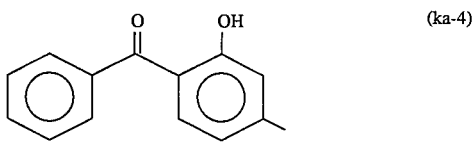

(ka-4)

In the formulas (1), (2) and (3), each of $X^1$, $X^2$, $X^3$, $X^4$ and $X^5$ is a single bond or an oxygen atom, preferably an oxygen atom. $X^2$ and $X^3$, $X^4$ and $X^5$, may be the same or different from each other, but they are preferably the same.

$Q^1$ is a single bond or a bivalent linking group having a carbon atom directly bonded to $X^1$, preferably the bivalent linking group. When both $Q^1$ and $X^1$ are single bonds, $R_f^1$ and $\Phi^1$ are directly bonded. When $Q^1$ is a single bond, $X^1$ is preferably an oxygen atom.

Each of $Q^2$ and $Q^3$ is a single bond or a bivalent linking group. The bivalent linking group for $Q^2$ or $Q^3$ is not particularly limited and may be a bivalent linking group having a carbon atom, a nitrogen atom or a sulfur atom directly bonded to $X^2$ or $X^3$, preferably the one having a carbon atom directly bonded to $X^2$ or $X^3$. When both $Q^2$ and $X^2$ are single bonds, $\Phi^2$ and $R_f^2$ are directly bonded. Likewise, when both $Q^3$ and $X^4$ are single bonds, $R_f^2$ and $\Phi^3$ are directly bonded. When $Q^2$ is a single bond, $X^2$ is preferably an oxygen atom. Likewise, when $Q^3$ is a single bond, $X^3$ is preferably an oxygen atom. $Q^2$ and $Q^3$ may be the same or different, preferably the same. Particularly preferred is a case where $Q^2$ and $Q^3$ are the same bivalent linking groups.

Preferred as the bivalent linking group for $Q^1$, $Q^2$ and $Q^3$ is, for example, —$(CH_2)_p$—, —$(CH_2)_g$—$CH(OR^1)$—$(CH_2)_q$—, —$(CH_2)_r$—$N(R^2)SO_2$—, —$C(O)$—$(CH_2)_s$—, —$(CH_2)_a$—$COO$—$(CH_2)_b$—, —$(CH_2)_c$—$COO$—$(CH_2)_d$—$N(R^3)SO_2$— or —$(CH_2)_e$—$OCO$—$(CH_2)_f$—$N(R^4)SO_2$—, wherein p is an integer of from 1 to 11, each of g, q and s is an integer of from 0 to 11, r is an integer of from 2 to 11, each of a and c is an integer of from 0 to 8, each of b, d, e and f is an integer of from 1 to 8, $R^1$ is a hydrogen atom, a $C_{1-5}$ alkyl group or an acyl group, and each of $R^2$, $R^3$ and $R^4$ is a $C_{1-10}$ alkyl group.

Among them more preferred as $Q^1$, $Q^2$ and $Q^3$ is —$(CH_2)_p$—, —$(CH_2)_g$—$CH(OR^1)$—$(CH_2)_q$—, —$(CH_2)_a$—$COO$—$(CH_2)_b$—, —$(CH_2)_c$—$COO$—$(CH_2)_d$—$N(R^3)SO_2$— or —$(CH_2)_e$—$OCO$—$(CH_2)_f$—$N(R^4)SO_2$—, wherein p is an integer of from 2 to 8, g is an integer of from 0 to 8, q is an integer of from 1 to 8, each of a and c is an integer of from 0 to 6, each of b, d, g and f is an integer of from 1 to 8, $R^1$ is a hydrogen atom or an acyl group, and each of $R^3$ and $R^4$ is a $C_{1-3}$ alkyl group.

Particularly preferred as $Q^1$, $Q^2$ and $Q^3$ is —$(CH_2)_g$—$CH(OR^1)$—$(CH_2)_q$— wherein g is an integer of from 1 to 3, q is an integer of from 1 to 6, and $R^1$ is a hydrogen, —$(CH_2)_a$—$COO$—$(CH_2)_b$—, wherein a is an integer of from 0 to 3, and b is an integer of from 1 to 4, —$(CH_2)_c$—$COO$— $(CH_2)_d$—$N(R^3)SO_2$—, wherein c is an integer of from 1 to 3, d is an integer of from 2 to 4, and $R^3$ is a $C_{1-3}$ alkyl group, or —$(CH_2)_e$—$OCO$—$(CH_2)_f$—$N(R^4)SO_2$—, wherein e is an integer of from 1 to 3, f is an integer of from 2 to 4, and $R^4$ is a $C_{1-3}$ alkyl group.

$R_f^1$ in the formula (1) is a monovalent polyfluorohydrocarbon group. The carbon number of $R_f^1$ is usually from 2 to 22, preferably from 4 to 18, more preferably from 6 to 14. The number of fluorine atoms in $R_f^1$ is such that the proportion of the number of substituted fluorine atoms to the number of hydrogen atoms in a non-substituted hydrocarbon group is at least 50%, preferably at least 60%. Further, some or all of the unsubstituted hydrogen atoms may be substituted by chlorine atoms Further, $R_f^1$ may have a linear structure or a branched structure, preferably a linear structure. When it has a branched structure, the branched portion is preferably a short chain of from 1 to 4 carbon atoms.

$R_f^1$ is preferably a perfluorohydrocarbon of the formula $CF_3(CF_2)_z$— (wherein z is an integer of from 5 to 13) or of a structure wherein the terminal portion of $R_f^1$ is a perfluorohydrocarbon group.

$R_f^1$ may be a group having at least one unsaturated portion such as a carbon-carbon unsaturated double bond. Especially when $X^1$ is an oxygen atom, and $Q^1$ is a single bond, it is preferably a group having at least one unsaturated portion from the viewpoint of efficient synthesis. Otherwise, $R_f^1$ may be a polyfluorooxyhydrocarbon with some of the carbon atoms of $R_f^1$ substituted by ether oxygen atoms.

When $R_f^1$ is a group having at least one saturated portion such as a carbon-carbon unsaturated double bond, it preferably has one or two unsaturated portions. Particularly preferred is a polyfluoroalkenyl group having one unsaturated portion. As such a polyfluoroalkenyl group, a perfluoroalkenyl group wherein all hydrogen atoms bonded to carbon atoms are substituted by fluorine atoms. It is preferred that one of the unsaturated portions is located near the benzophenone structure of $R_f^1$.

The polyfluorooxyhydrocarbon group is preferably a group having at least one unit of polyfluorooxymethylene, polyfluorooxyethylene or polyfluorooxypropylene, more preferably a group having at least one unit of polyfluorooxypropylene. Particularly preferred is a group containing at least one unit of polyfluorooxypropylene and a perfluorohydrocarbon group at the terminal portion.

Specific examples of $R_f^1$ include $CF_3(CF_2)_7$—, $CF_3(CF_2)_9$—, $CF_3(CF_2)_{11}$—, $(CF_3)_2CF(CF_2)_5$—, $HCF_2(CF_2)_7$—, $ClCF_2(CF_2)_9$—, $CF_3(CF_2)_3(CH_2CF_2)_7$—, $C_8F_{17}(CH_2CF_2)_v$— wherein v is an integer of from 1 to 4, $CH_3CF_2(CH_2CF_2)_7$—, $C_6F_{13}(CH_2CF_2)_3$—, $CF_3(CF_2)_3(CFClCF_2)_7$—, $CF_3(CF_2)_3(CFHCF_2)_7$—, $(CF_3)_2CF(CF_2)_4$—, $(CF_3)_2CFCF=C(CF_3)$—, $(CF_3)_2C=C(C_2F_5)$—, $CF_3CF_2C(C_2F_5)(CF_3)$—$C(CF_3)=C(CF_3)$—, $CF_3CF=CFCF_2CF=CF$—, $(C_3F_7)(CF_3)C=C\{CF(CF_3)_2\}$—, $CF_2ClCFClCF_2CF_2\{OCF(CF_3)CF_2\}_wOCF(CF_3)$— wherein w is an integer of from 1 to 4, $C_3F_7$—$\{OCF(CF_3)CF_2\}_{j-}$$O(CF_2)_2$— wherein j is an integer of from 1 to 4, and examples in the specific compounds.

$R_f^2$ in the formula (2) is a bivalent polyfluorohydrocarbon group The structure of $R_f^2$ is the same as the structure of the above $R_f^1$, provided that one terminal atom of $R_f^1$ is substituted by a single bond. The carbon number of $R_f^2$ is from 2 to 22, preferably from 4 to 10. $R_f^2$ may, for example, be a polyfluoroalkylene group, a polyfluoroalkylene group having at least one carbon-carbon unsaturated double bond, or a polyfluorooxyalkylene group.

Specific examples of $R_f^2$ include —$(CH_2)_8$—, —$(CH_2)_4$—, —$(CF_2CH_2)_2(CF_2)_2(CH_2CF_2)_2$—, —$(CF_2CHCl)_2(CF_2)_2(CHClCF_2)_2$—, —$(CF_2O)_h(C_2F_4O)_i$—, —$(CF_2)_2O$—$\{CF_2CF(CF_3)O\}_t(CF_2)_2\{OCF(CF_3)CF_2\}_u$—$O(CF_2)_2$—, wherein each of h, i, t and u is an integer of from 1 to 4, provided that $(3t+3u) \leq 16$, —$(CF_2CH_2)_2C_6F_{12}(CH_2CF_2)_2$—, —$C_2F_4O\{CF_2CF(CF_3)O\}_2CF_2CF_2\{OCF(CF_3)CF_2\}_2OC_2F_4$— and examples in the specific compounds.

$Q_f$ in the formula (3) is a bivalent linking group having at least one $Q^4$—$R_f^1$. As such $Q_f$, a bivalent linking having one $Q^4$—$R_f^1$ is preferred Here, $Q^4$ is a bivalent linking group, which is the same as the bivalent linking group for the above $Q^2$ and $Q^3$. $R_f^1$ is as defined above.

The residue of (2+A) valency (wherein A is the number of $Q^4$—$R_f^1$ contained in $Q_f$) having $Q^4$—$R_f^1$ removed from $Q_f$, is preferably a hydrocarbon group, a hydrocarbon group having at least one hydroxyl group, or a hydrocarbon group containing at least one ester bond. For example, when $Q_f$ has one $Q^4$—$R_f^1$, the residue excluding $Q^4$—$R_f^1$ is preferably a trivalent hydrocarbon group, a trivalent hydrocarbon group containing at least one hydroxyl group, or a trivalent hydrocarbon group containing at least one ester bond.

When the residue excluding $Q^4$—$R_f^1$ in the case of one $Q^4$—$_{R_f^1}$, is a trivalent hydrocarbon group, the carbon number of such a trivalent hydrocarbon group is preferably from 3 to 5. Particularly preferred is a hydrocarbon group having 3 carbon atoms. When it is a trivalent hydrocarbon group containing at least one hydroxyl group, preferred is a hydrocarbon group containing two hydroxyl groups. When it is trivalent hydrocarbon group containing at least one ester bond, preferred is a hydrocarbon group containing two ester bonds.

$Q_f$ having one $Q^4$—$R_f^1$ is preferably a bivalent linking group of the formula (4):

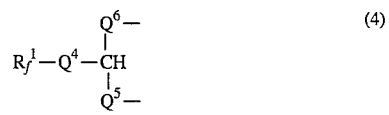

In the formula (4), $R_f^1$ is as defined above, and $Q^4$ is the same as the above $Q^2$ and $Q^3$, preferably a bivalent linking group. $Q^4$ is preferably —$(CH_2)_p$— where p is an integer of from 2 to 8, and $R_f^1$ is preferably $CF_3(CF_2)_z$— wherein z is an integer of from 5 to 13.

Each of $Q^5$ and $Q^6$ is the same bivalent linking group as the bivalent linking group for the above $Q^2$ and $Q^3$, preferably a bivalent hydrocarbon group, a bivalent hydrocarbon group having two hydroxyl groups, or a bivalent hydrocarbon group containing two ester bonds. $Q^5$ and $Q^6$ may be the same or different, preferably the same. Each of $Q^5$ and $Q^6$ is preferably —$(CH_2)_p$— wherein p is 1, —$(CH_2)_g$—$CH(OR_1)$—$(CH_2)_q$— wherein g is an integer of 0 or 1, q is an integer of 1 or 2, and $R^1$ is a hydrogen, or —$(CH_2)_a$—COO—$(CH_2)_b$— wherein a is an integer of 0 or 1, and b is an integer of from 1 to 6, particularly preferably —$(CH_2)_a$—COO—$(CH_2)_b$— wherein a is 0, and b is an integer of from 1 to 4.

Specific examples of the formula (4) will be given, but it is by no means restricted to such specific examples.

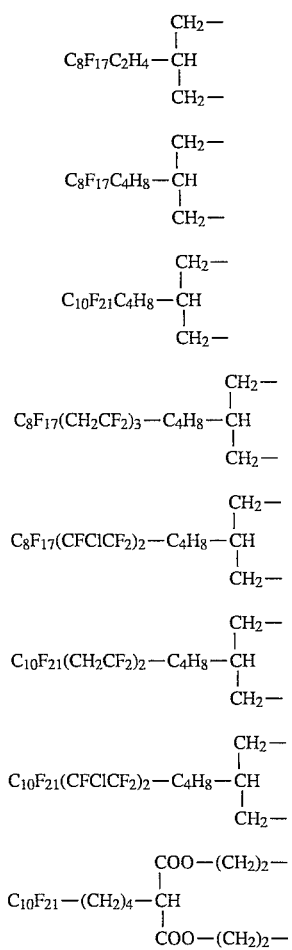

-continued $$C_8F_{17}-(CH_2)_4-\overset{\overset{\displaystyle COO-(CH_2)_2-}{|}}{\underset{\underset{\displaystyle COO-(CH_2)_2-}{|}}{CH}}$$

$$C_{10}F_{21}-(CH_2)_2-\overset{\overset{\displaystyle COO-(CH_2)_2-}{|}}{\underset{\underset{\displaystyle COO-(CH_2)_2-}{|}}{CH}}$$

$$C_8F_{17}-(CH_2)_2-\overset{\overset{\displaystyle COO-(CH_2)_3-}{|}}{\underset{\underset{\displaystyle COO-(CH_2)_3-}{|}}{CH}}$$

$$C_8F_{17}-(CH_2CF_2)_3-(CH_2)_4-\overset{\overset{\displaystyle COO-(CH_2)_2-}{|}}{\underset{\underset{\displaystyle COO-(CH_2)_2-}{|}}{CH}}$$

-continued $$C_8F_{17}-(CFClCF_2)_2-(CH_2)_4-\overset{\overset{\displaystyle COO-(CH_2)_2-}{|}}{\underset{\underset{\displaystyle COO-(CH_2)_2-}{|}}{CH}}$$

Now, examples of specific compounds will be given for the fluorine-containing benzophenone derivatives of the present invention. However, the compounds of the present invention are not limited to such specific examples.

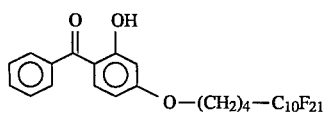

(5)

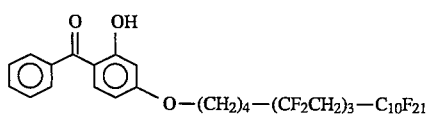

(6)

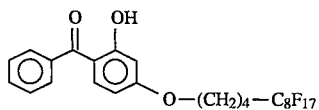

(7)

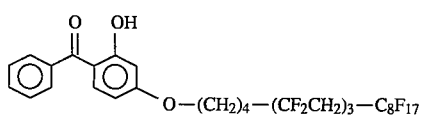

(8)

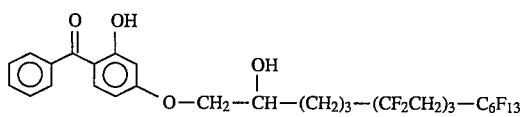

(9)

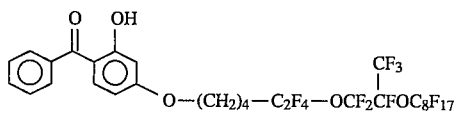

(10)

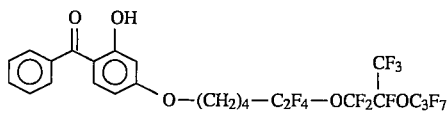

-continued
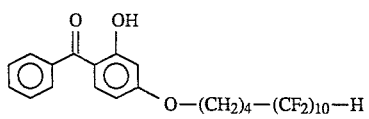
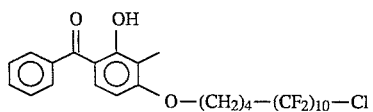
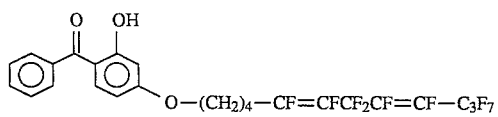
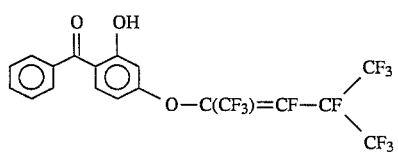
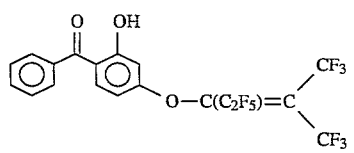
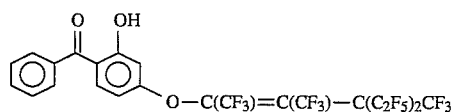
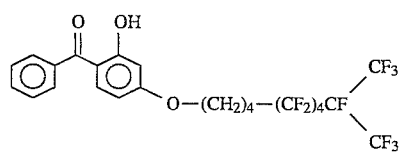
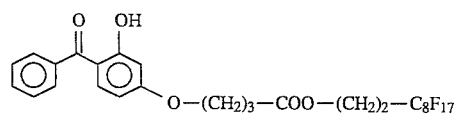
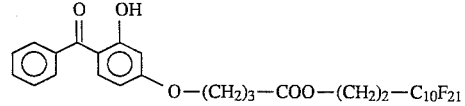
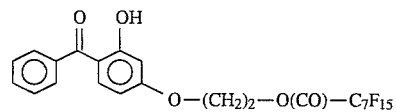
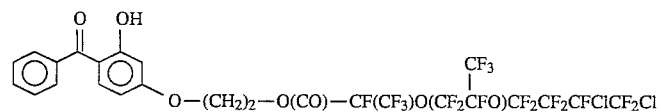
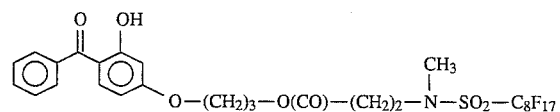
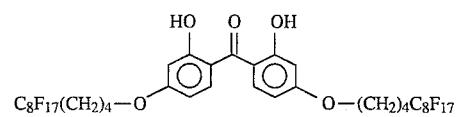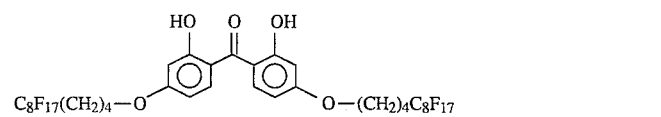

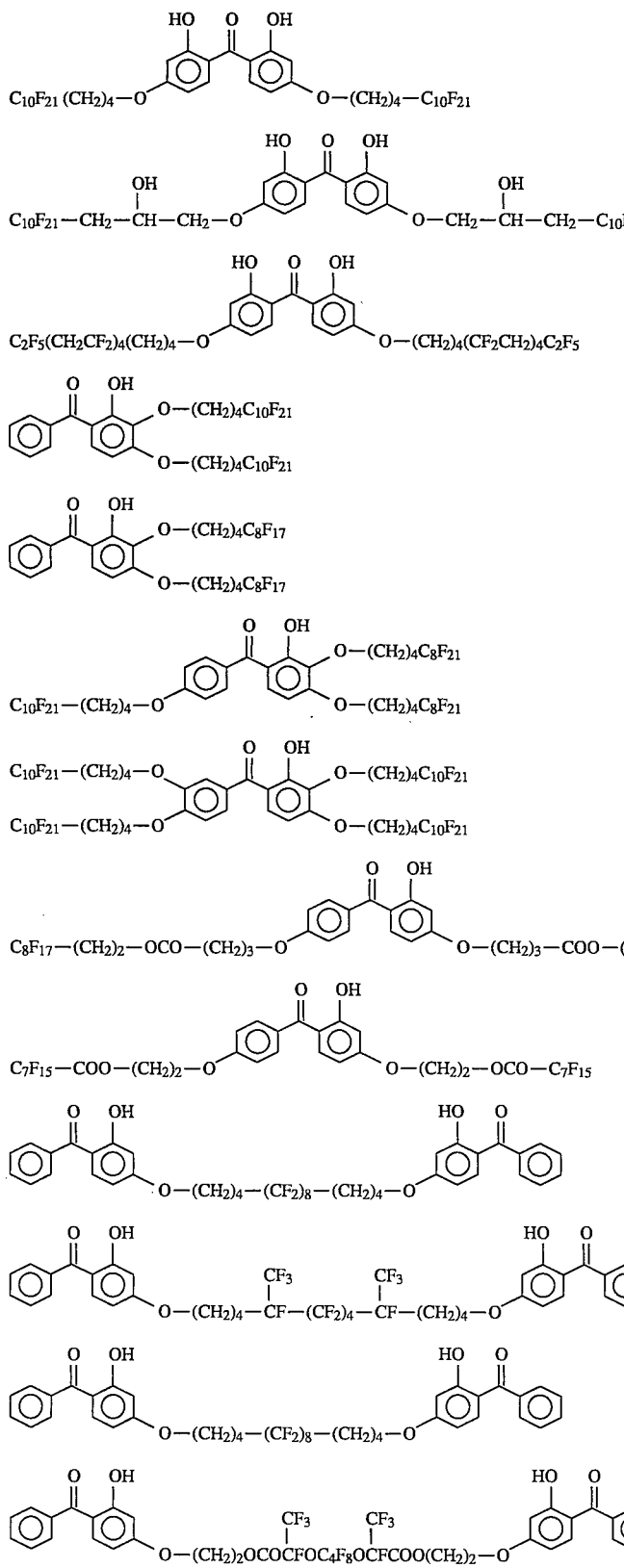

-continued
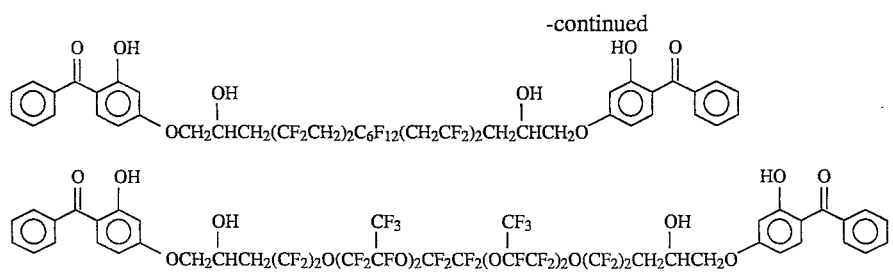
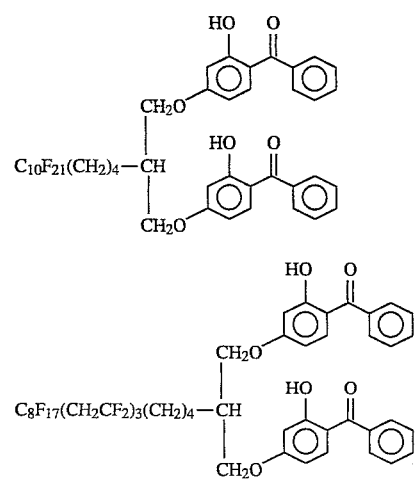
(11)
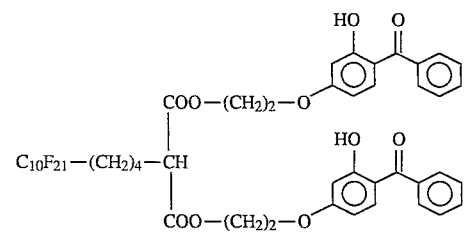
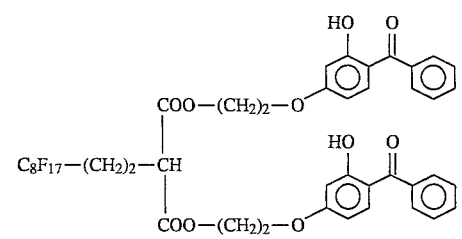
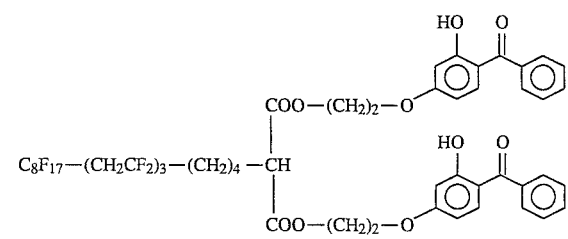
(12)

-continued

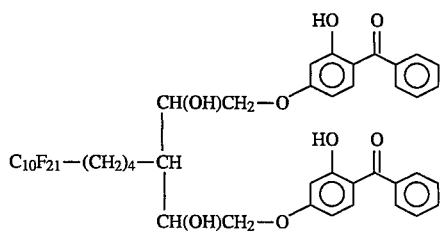

The fluorine-containing benzophenone derivative of the present invention can be synthesized by a conventional organic synthetic method. For example, it can be synthesized by reacting a benzophenone containing a hydroxyl group with $R_f^1$—$Q^1$—$Z^1$, $Z^2$—$Q^2$—$R_f^2$—$Q^3$—$Z^3$ or $Z^4$—$Q^5$—$Q_f$—$Q^6$—$Z^5$ wherein each of $Z^1$ to $Z^5$ is an iodine atom, a bromine atom or a chlorine atom, and $Q^1$, $Q^2$, $Q^3$, $Q^5$, $Q^6$, $R_f^1$, $R_f^2$ and $Q_f$ are as defined above. Further, by reacting a 3-substituted 1,2-epoxypropane having $R_f^1$ bonded at the 3-position, with a benzophenone containing a hydroxyl group, a fluorine-containing benzophenone derivative wherein $Q^1$ is —$CH_2CH(OH)$—$CH_2$— can be prepared. Likewise by reaction a polyfluoroalkene having at least one fluorine atom bonded to the carbon atoms of a carbon-carbon unsaturated double bond, with a benzophenone containing a hydroxyl group, a fluorine-containing benzophenone derivative wherein $X^1$ is an oxygen atom, $Q^1$ is a single bond and $R_f^1$ is a polyfluoroalkenyl group containing one carbon-carbon unsaturated double bond, can be prepared.

The above reactions can be carried out in an organic solvent under a basic condition.

As the organic solvent, a polar solvent is preferred, and a solvent of ether type, alcohol type or ester type, may be employed. For example, it may be ethylene glycol, ethylene glycol monomethyl ether, diethylene glycol monoethyl ether, diethylene glycol dimethyl ether, methanol, ethanol, isopropanol, tetrahydrofuran or ethyl acetate.

As the base, an alkali metal carbonate or hydroxide may, usually, be employed. For example, it may be sodium carbonate, potassium carbonate, sodium hydrogencarbonate, sodium hydroxide, potassium hydroxide or cesium hydroxide.

The reaction conditions may vary depending upon the compounds used as the starting materials, the types or amounts of the solvent and the base, etc. However, usually, the reaction temperature is from 0° to 200° C., and the reaction time is from 0.5 to 50 hours.

The fluorine-containing benzophenone derivatives of the present invention have absorptivity at a wavelength of at most 300 nm and thus are useful as ultraviolet absorbers. Further, they have polyfluorohydrocarbon groups in their molecules, the decomposition points or sublimation points are high at a level of at least 200° C., and thus they are excellent ultraviolet absorbers having higher heat resistance than conventional compounds. Accordingly, the fluorine-containing benzophenone derivatives of the present invention can be used for various applications as ultraviolet absorbers.

The fluorine-containing benzophenone derivatives of the present invention can be used for incorporation to various resins to impart ultraviolet absorptivity to such resins. In particular, by kneading a fluorine-containing benzophenone derivative of the present invention into a resin at the time of molding the resin, it is possible to obtain a molded product of a resin having ultraviolet ray absorptivity imparted thereto. In this case, the type of the resin is not particularly limited, and the derivative of the present invention can be applied to various resins. The fluorine-containing benzophenone derivatives of the present invention have particularly high heat resistance, and can be incorporated to thermoplastic resins. As such thermoplastic resins, polyethylene, polyvinyl chloride, polystyrene, polymethyl methacrylate and polycarbonate may, for example, be mentioned.

Further, the fluorine-containing benzophenone derivatives of the present invention have polyfluorohydrocarbons in their molecules, and thus they have excellent compatibility with fluorine resins. Accordingly, they can be incorporated to fluorine resins to which conventional ultraviolet absorbing compounds can hardly be incorporated, and yet they have high heat resistance. Therefore, it is possible to incorporate them by kneading them at the time of molding the fluorine resins.

Such a fluorine resin may, for example, be a homopolymer of a fluorine-containing monomer such as tetrafluoroethylene, vinylidene fluoride, chlorotrifluoroethylene, vinyl fluoride, polyfluoroalkylethylene or polyfluoroalkylvinyl ether, or a copolymer obtained by polymerizing two or more such fluorine-containing monomers. Otherwise, the fluorine resin may be a copolymer of one or more such fluorine-containing monomers with one or more other polymerizable monomers, or a cyclic perfluoropolymer. Other polymerizable monomers are not particularly limited, and conventional polymerizable monomers may be employed. For example, ethylene, propylene, butadiene, an alkylvinyl ester or an alkylvinyl ether is preferred. These fluorine resins may be crystalline or non-crystalline.

The amount of the fluorine-containing benzophenone derivative of the present invention to be incorporated to the resin is usually from 0.001 to 20 wt %, preferably from 0.01 to 10 wt %.

There is no particular-restriction as to the molded product of a resin having the fluorine-containing benzophenone derivative of the present invention incorporated. Various molded products are possible. The fluorine-containing benzophenone derivatives of the present invention are particularly excellent in the heat resistance, and therefore they may be incorporated to fluorine resins which require high temperature molding to obtain molded products of fluorine resins having ultraviolet absorptivity imparted thereto. As such fluorine resin molded products, various surface protecting films on which ultraviolet shielding properties are required, may be mentioned, including, for example, tubes for covering transmission cables, filters, sheets, ultraviolet ray shielding films for liquid crystals and protecting films for marking films. It is particularly advantageous that when incorporated to a fluorine resin to form a transparent film, the fluorine-containing benzophenone derivative of the present invention is capable of imparting ultraviolet absorptivity without impairing the transparency of the resin.

Further, a molded product of the resin containing the fluorine-containing benzophenone derivative of the present invention is excellent also in the weather resistance by virtue of the effects of the polyfluorohydrocarbon groups present at the resin surface.

Now, the present invention will be described in further detail with reference to Examples. However, it should be understood that the present invention is by no means restricted to such specific Examples.

EXAMPLE 1

3 g of 2,4-dihydroxybenzophenone, 10 g of n-$C_{10}F_{21}C_4H_8I$, and 1.4 g of sodium hydrogencarbonate were dissolved in 50 ml of methyl cellosolve. The temperature was gradually raised, and the solution was heated at 120° C. for 3 hours. After completion of the reaction, the reaction solution was cooled to room temperature and poured into a large amount of water. A formed precipitate was collected by filtration, washed with water and dried to obtain crude crystals. The obtained crude crystals were recrystallized from 1,1,2-trichloro-1,2,2-trifluoroethane (hereinafter referred to simply as R-113) to obtain white crystals of 2-hydroxy-4-(4-perfluorodecylbutoxy)benzophenone. The amount was 3.4 g, and the yield of 29.8%.

$^1$H-NMR(TMS,CDCl$_3$)δ (ppm): 1.2–2.6(6H,m) 4.1(2H,t), 6.3–7.9(8H,m).

$^{19}$F-NMR(CFCl$_3$,CDCl$_3$)δ (ppm): −81.4(3F,t), −115.8(2F,s), −122.0–124.5(14F,m), −126.4(2F,s).

The obtained white crystals were dissolved in chloroform (concentration: 5×10$^{-5}$ mols/l), and the absorption wavelength and the intensity were measured by a spectrophotometer (UV-2200, manufactured by Shimadzu Corporation). As a result, the maximum absorption wavelength (hereinafter referred to simply as $\lambda_{max}$) was 287 nm, and the molar absorbance coefficient (hereinafter referred to simply as ε) was 1.6×10$^4$. Further, a thermogravimetric analysis of the obtained compound was conducted. The analysis was carried out in such a manner that the sample was heated at a rate of 10° C./min from room temperature, and the temperature at which the mass of the sample decreased by 10%, was measured. The 10% weight decrease temperature (hereinafter referred to simply as $T_d$) was 270° C.

EXAMPLES 2 to 9

Fluorine-containing benzophenone derivatives were synthesized in the same manner as in Example 1 except that starting materials as identified in Table 1 were used instead of n-$C_{10}F_{21}C_4H_8I$ used in Example 1. The yield, $\lambda_{max}$, ε and $T_d$ after purification are shown in Table 1.

The compound synthesized in Example 2 by the reaction of the epoxy group-containing compound as identified in Table 1 with 2,4-dichydroxybenzophenone, is shown by the formula ka-15. $^1$H-NMR and $^{19}$F-NMR of the compound of the formula ka-15 were measured, and the results are as follows.

$^1$H-NMR(TMS,CDCl$_3$)δ (ppm): 2.6(2H,t), 4.2(2H,s), 4.5(1H,m), 6.3–7.9(8H,m).

19F-NMR(CFCl$_3$,CDCl$_3$) (ppm): −81.2( 3F,t), −115.6(2F,s), −122.0–124.4(14F,m), −126.3(2F,s).

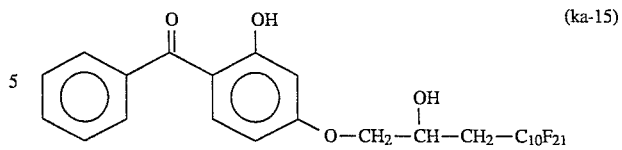
(ka-15)

The compound synthesized in Example 5 by the reaction of the epoxy group-containing compound as identified in Table 1 with 2,4-dihydroxybenzophenone is shown by the formula ka-16.

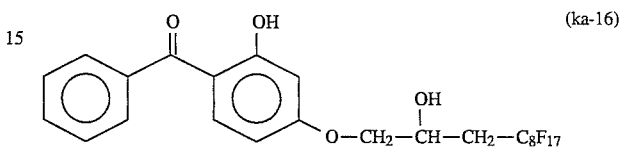
(ka-16)

1H-NMR and $^{19}$F-NMR of the compound synthesized in Example 6 as identified in Table 1 were measured, and the results are as follows. $^1$H-NMR(TMS,CDCl$_3$)δ (ppm): 1.4–3.2(12H,m), 4.1(2H,s), 6.3–7.8(8H,m).

$^{19}$F-NMR(CFCl$_3$,CDCl$_3$)δ (ppm): −81.3(3F,t), −88.6(2F,s), −90.8(2F,s), −95.0(2F,s), −112.8(2F,s), −122.0–139.9(10F,m), −126.6(2F,s).

EXAMPLE 10

3.2 g of diethyl malonate was dissolved in 100 ml of tetrahydrofuran (hereinafter referred to simply as THF), and 0.6 g of NaH was added thereto. Then, 14 g of n-$C_{10}F_{21}C_4H_8I$ was added thereto. The temperature was raised from room temperature to 60° C., and the mixture was stirred for 1 hour. Then, a formed precipitate was collected by filtration and washed to obtain 12 g of diethyl 2-(4-perfluorodecylbutyl)malonate. This product was reduced with 1.2 g of aluminum lithium hydride and then reacted with 6.8 g of thionyl chloride to obtain 4 g of 1,3-dichloro-2-(4-perfluorodecylbutyl)propane.

Such 1,3-dichloro-2-(4-perfluorodecylbutyl)propane and 2.73 g of 2,4-dihydroxybenzophenone were dissolved in 30 ml of 2-methoxyethanol, and 1.2 g of sodium carbonate, 1.0 g of sodium hydrogencarbonate and 0.5 g of potassium iodide were added thereto. The mixture was reacted at 120° C. for 20 hours. The reaction solution was poured into 200 ml of water/ethanol=1/1 (volume ratio), whereupon a formed precipitate was collected by filtration and purified to obtain 1,3-bis-(4-benzoyl-3-hydroxyphenoxy)-2-(4-perfluorodecylbutyl)propane. The yield, $\lambda_{max}$, ε and $T_d$ after purification are shown in Table 1.

EXAMPLE 11

A fluorine-containing benzophenone derivative was synthesized in the same manner as in Example 10 except that n-$C_8F_{17}(CH_2CF_2)_3C_4H_8I$ was used instead of n-$C_{10}F_{21}C_4H_8I$ used in Example 10. The yield, $\lambda_{max}$, ε and $T_d$ after purification are shown in Table 1.

TABLE 1

| Ex. | Starting material | Product | Yield | $\lambda_{max}$ | $\epsilon$ | $T_d$ |
|---|---|---|---|---|---|---|
| 2 | $C_{10}F_{21}-CH_2-CH\underset{O}{\overset{}{\diagup\!\!\!\!\diagdown}}CH_2$ | ka-15 | 55% | 290 nm | $1.3 \times 10^4$ | 285° C. |
| 3 | $C_{10}F_{21}-(CH_2-CF_2)_3-C_4H_8-I$ | ka-9 (5) | 29% | 287 nm | $1.5 \times 10^4$ | 297° C. |
| 4 | $C_8F_{17}-C_4H_8-I$ | ka-9 (6) | 33% | 287 nm | $1.5 \times 10^4$ | 260° C. |
| 5 | $C_8F_{17}-CH_2-CH\underset{O}{\overset{}{\diagup\!\!\!\!\diagdown}}CH_2$ | ka-16 | 37% | 290 nm | $1.3 \times 10^4$ | 283° C. |
| 6 | $C_8F_{17}-(CH_2-CF_2)_3-C_4H_8-I$ | ka-9 (7) | 33% | 287 nm | $1.4 \times 10^4$ | 296° C. |
| 7 | $C_3F_7OCF(CF_3)CF_2OC_2F_4-C_4H_8-I$ | ka-10 (8) | 35% | 287 nm | $1.6 \times 10^4$ | 214° C. |
| 8 | $C_2F_5-(CH_2-CF_2)_4-C_4H_8-I$ | ka-10 (9) | 23% | 287 nm | $1.5 \times 10^4$ | 300° C. |
| 9 | $C_6F_{13}(CH_2-CF_2)_3(CH_2)_3CH\underset{O}{\overset{}{\diagup\!\!\!\!\diagdown}}CH_2$ | ka-9 (10) | 27% | 290 nm | $1.4 \times 10^4$ | 292° C. |
| 10 | $C_{10}F_{21}C_4H_8CH\begin{subarray}{l}CH_2Cl\\ \\CH_2Cl\end{subarray}$ | ka-14 (11) | 57% | 284 nm | $2.3 \times 10^4$ | 278° C. |
| 11 | $C_8F_{17}(CH_2CF_2)_3C_4H_8CH\begin{subarray}{l}CH_2Cl\\ \\CH_2Cl\end{subarray}$ | ka-14 (12) | 48% | 287 nm | $2.3 \times 10^4$ | 292° C. |

EXAMPLE 12

Into a 500 cc three-necked flask equipped with a water separator, 102 g of $C_{10}F_{21}(CH_2)_2OH$, 24 g of $Cl(CH_2)_3COOH$, 3.5 g of p-toluenesulfonic acid and 100 cc of toluene were charged, and the mixture was refluxed at 120° C. for 5 hours. Then, water was azeotropically separated. Toluene was recovered under reduced pressure to obtain 114.3 g (yield: 95%) of an ester. 114.3 g of the obtained ester and 224.7 g of 2,4-dihydroxybenzophenone were dissolved in 100 g of diglyme, and 28.9 g of sodium hydrogencarbonate as a catalyst and 4.3 g of potassium iodide were added thereto. The mixture was reacted at 120° C. for 4 hours. The reaction solution was poured into 400 cc of water, whereupon the solid was recovered and washed with ethanol to obtain 117.9 g of a compound of the formula ka-17. The yield, $\lambda_{max}$, $\epsilon$ and $T_d$ after purification are shown in Table 2. Further, $^1$H-NMR and $^{19}$F-NMR of the compound of the formula ka-17 were measured, and the results are as follows.

$^1$H-NMR(TMS,CDCl$_3$)δ (ppm): 2.3(2H,m), 2.6(4H,m), 4.1(2H,t), 4.5(2H,t), 6.5–7.5(8H,m).

$^{19}$F-NMR(CFCl$_3$,CDCl$_3$)δ (ppm): −81.3(3F,t), −114.0(2F, m), −122.3–124.1(14F,m), −126.6(2F,s).

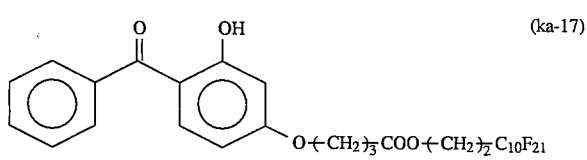

(ka-17)

EXAMPLE 13

A compound of the formula ka-18 was prepared in the same manner as in Example 12 except that $C_{10}F_{21}(CH_2)_2OH$ in Example 12 was changed to $C_8F_{17}(CH_2)_2OH$. The yield, $\lambda_{max}$, $\epsilon$ and $T_d$ after purification are shown in Table 2.

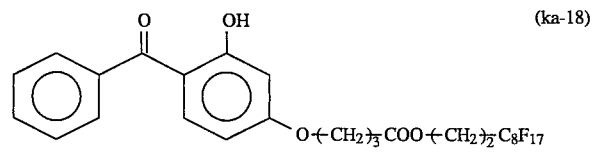

(ka-18)

EXAMPLE 14

A compound of the formula ka-19 was prepared in the same manner as in Example 12 except that $C_{10}F_{21}(CH_2)_2OH$ in Example 12 was changed to $C_8F_{17}SO_2N(CH_3)(CH_2)_2OH$. The yield, $\lambda_{max}$, $\epsilon$ and $T_d$ after purification are shown in Table 2.

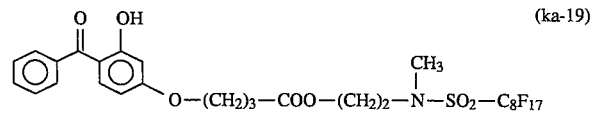

(ka-19)

EXAMPLE 15

Into a 100 cc three-necked flask equipped with a refluxed condenser, 3 g of 2-hydroxy-4-(2-hydroxyethoxy)benzophenone and 10 cc of THF were charged, and 5.4 g (1.1 equivalent) of $C_7F_{15}COF$ was dropwise added thereto with stirring. The mixture was reacted at room temperature for 2 hours, and then extracted with R-113 by an addition of water. The R-113 layer was recovered, and the solvent was distilled off to obtain a compound of the formula ka-20. The yield, $\lambda_{max}$, $\epsilon$ and $T_d$ after purification are shown in Table 2.

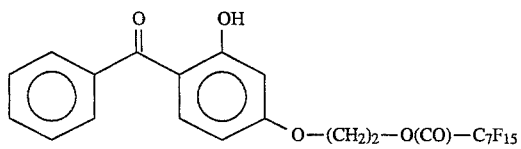
(ka-20)

EXAMPLE 16

Instead of $C_7F_{15}COF$ in Example 15, 6.2 g of $F(CO)CF(CF_3)OC_4F_8OCF(CF_3)COF$ was used and reacted with 5.8 g of 2-hydroxy-4-(2-hydroxyethoxy)benzophenone in the same manner. After distilling R-113 off, a compound of the formula ka-21 was obtained as a viscous liquid. The yield, $\lambda_{max}$, $\epsilon$ and $T_d$ after purification are shown in Table 2.

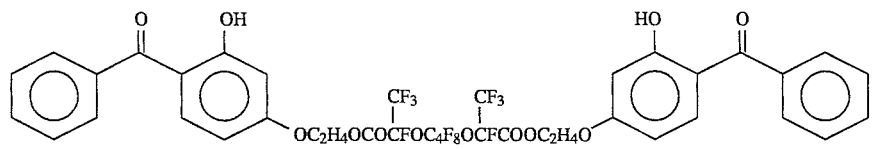
(ka-21)

EXAMPLE 17

Into a 500 cc three-necked flask equipped with a dropping funnel and a reflux condenser, 33.6 g of diethyl malonate and 50 g of THF were charged and cooled on ice bath. Then, 12.4 g of sodium methoxide was gradually added thereto. The mixture was stirred at room temperature for 1 hour, and then a solution having 114.8 g of $C_8F_{17}(CH_2)_2I$ dissolved in 100 g of THF, was added thereto all at once from the dropping funnel. Then, the temperature was raised to 65° C., and refluxing was conducted for 1 hour. The reaction product was cooled to room temperature. Then, the solid was removed by filtration, and THF was further distilled off. The obtained composition was dissolved in R-113 and purified by silica gel column chromatography to obtain a transparent liquid. Low boiling substances were removed under reduced pressure to obtain 82 g of a diester. The purity was 90%.

Into a 200 cc three-necked flask, 82 g of the diester, 59.4 g of 2-hydroxy-4-ethoxybenzophenone and 4.3 g of p-toluenesulfonic acid were introduced and reacted at 120° C. for 20 hours under a condition of 10 mmHg with stirring. Then, the mixture was cooled to 40° C., and 300 g of R-113 was added thereto. The mixture was washed with water. The R-113 layer was cooled, and a precipitated solid was collected by filtration. This solid was washed with ethanol and then dried to obtain 55.8 g of a compound of the formula ka-22. The yield, $\lambda_{max}$, $\epsilon$ and $T_d$ after purification are shown in Table 2. Further, $^1$H-NMR and $^{19}$F-NMR of the compound of the formula ka-22 were measured, and the results are as follows.

$^1$H-NMR(TMS,CDCl$_3$)$\delta$ (ppm): 1.7–2.6(4H,m), 3.5(1H,m), 4.2(4H,m), 4.5(4H,m), 6.3–7.5(16H,m).

$^{19}$F-NMR(CFCl$_3$,CDCl$_3$)$\delta$ (ppm): –81.3(3F,t), –114.9(2F,m), –122.2–123.6(10F,m), –126.6(2F,s).

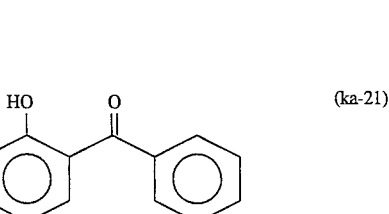
(ka-22)

EXAMPLE 18

A compound of the formula ka-23 was prepared in the same manner as in Example 5 except that $C_8F_{17}(CH_2)_2I$ in Example 5 was changed to $C_{10}F_{21}(CH_2)_4I$. The yield, $\lambda_{max}$, $\epsilon$ and $T_d$ after purification are shown in Table 2.

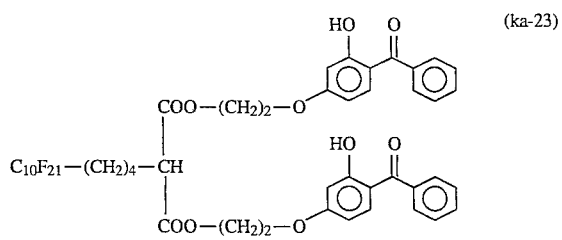
(ka-23)

TABLE 2

| Ex. | Starting material | Product | Yield | $\lambda_{max}$ | $\epsilon$ | $T_d$ |
|---|---|---|---|---|---|---|
| 12 | $C_{10}F_{21}(CH_2)_2OC(O)(CH_2)_3Cl$ | ka-17 | 81% | 287 nm | $1.5 \times 10^4$ | 280° C. |
| 13 | $C_8F_{17}(CH_2)_2OC(O)(CH_2)_3Cl$ | ka-18 | 83% | 287 nm | $1.4 \times 10^4$ | 265° C. |
| 14 | $C_8F_{17}SO_2N(CH_3)(CH_2)_2OCO(CH_2)_3Cl$ | ka-19 | 80% | 288 nm | $1.6 \times 10^4$ | 318° C. |

TABLE 2-continued

| Ex. | Starting material | Product | Yield | $\lambda_{max}$ | $\epsilon$ | $T_d$ |
|---|---|---|---|---|---|---|
| 15 | $C_7F_{15}COF$ | ka-20 | 98% | 285 nm | $1.6 \times 10^4$ | 309° C. |
| 16 | $\underset{\underset{CF_3}{\vert}}{FCCFOC_4F_8OCFCF} \\ \phantom{FCCFO}\overset{\Vert}{O}\phantom{C_4F_8O}\overset{\Vert}{O}$ | ka-21 | 80% | 285 nm | $3.2 \times 10^4$ | 310° C. |
| 17 | $C_8F_{17}(CH_2)_2\underset{\underset{COOC_2H_5}{\vert}}{\overset{\overset{COOC_2H_5}{\vert}}{CH}}$ | ka-22 | 31% | 285 nm | $3.0 \times 10^4$ | 315° C. |
| 18 | $C_{10}F_{21}(CH_2)_4\underset{\underset{COOC_2H_5}{\vert}}{\overset{\overset{COOC_2H_5}{\vert}}{CH}}$ | ka-23 | 33% | 287 nm | $3.3 \times 10^4$ | 320° C. |

COMPARATIVE EXAMPLE 1

$T_d$ of 2-hydroxy-4-(2'-vinyloxyethoxy)benzophenone was measured, whereby this compound underwent decomposition at 157° C.

EXAMPLE 19

1.6 g of crystals of the fluorine-containing benzophenone derivative synthesized in Example 1 was dissolved in 50 ml of THF, and 20 g of a fluorine resin powder (a copolymer of tetrafluoroethylene with ethylene) was suspended therein. THF was distilled off, and then the fluorine resin powder was recovered. This fluorine resin powder was maintained in a Flowtester (Flowtester/FT-300, manufactured by Shimadzu Corporation) at 250° C. for 5 minutes, whereupon the mixture was extruded. This operation was repeated three times to obtain a composition comprising the fluorine resin and the fluorine-containing benzophenone derivative. Further, the composition was pressed at 250° C. under 200 atm for 5 minutes to form a film having a thickness of 50 μm.

The appearance of the formed film was transparent, and the transmittance of visible lights of at least 400 nm was at least 80%, and ultraviolet rays of at most 350 nm were completely shielded. FIG. 1 is a graph showing the light transmittance of the formed film plotted against the wavelength of light.

EXAMPLES 20 to 34

Fluorine resin films were prepared in the same manner as in Example 11 except that the fluorine-containing benzophenone derivative was changed to the compounds synthesized in Examples 2 to 10, 12 to 15, 17 and 18. The light transmittance of the films at 350 nm, 400 nm and 600 nm is shown in Table 3.

TABLE 3

| Example | Fluorine-containing benzophenone derivative | Light transmittance (%) at each wavelength | | |
|---|---|---|---|---|
| | | 330 nm | 400 nm | 600 nm |
| 20 | Example 2 | 0 | 82 | 91 |
| 21 | Example 3 | 0 | 85 | 92 |
| 22 | Example 4 | 1 | 85 | 90 |
| 23 | Example 5 | 0 | 83 | 89 |
| 24 | Example 6 | 0 | 85 | 90 |
| 25 | Example 7 | 3 | 80 | 88 |
| 26 | Example 8 | 0 | 82 | 90 |
| 27 | Example 9 | 0 | 84 | 90 |
| 28 | Example 10 | 0 | 83 | 90 |
| 29 | Example 12 | 0 | 80 | 90 |
| 30 | Example 13 | 0 | 83 | 91 |
| 31 | Example 14 | 0 | 83 | 90 |
| 32 | Example 15 | 0 | 85 | 91 |
| 33 | Example 17 | 0 | 78 | 85 |
| 34 | Example 18 | 0 | 79 | 85 |

COMPARATIVE EXAMPLE 2

A fluorine resin film was prepared in the same manner as in Example 11 except that 4-octyloxy-2-hydroxybenzophenone was used instead of the fluorine-containing benzophenone derivative of Example 11. The film had turbidity and was non-uniform.

COMPARATIVE EXAMPLE 3

A fluorine resin film was prepared in the same manner as in Example 11 except that a 1/1 (mol) copolymer of $C_8F_{18}CH_2CH_2$—$OCOCH\!=\!CH_2$ with benzophenone methacryl monomer ("Adecastub LA-22", manufactured by Asahi Denka K.K.) was used instead of the fluorine-containing benzophenone derivative of Example 11. The film had turbidity and was non-uniform.

EXAMPLES 35 to 38

Using the films prepared in Examples 20, 23, 29 and 34, accelerated weather resistance tests were conducted by means of Sunshine Weather-O-meter. For the accelerated weather resistance tests, Sunshine Weather-O-meter, manufactured by Suga Shikenki K.K. as prescribed in JIS B-7753 was used. The accelerated weather resistance tests were conducted under the conditions prescribed in JIS-K-5400 i.e. by maintaining the black panel temperature at a level of 60°±3° C., and an accelerated weather resistance test of 120 minutes per cycle (18 minutes thereof being under a raining condition) was conducted for 1000 hours, and the ultraviolet absorptivity of the film before and after the test was measured. The results are shown in Table 4.

TABLE 4

| Example | Film tested | Initial light transmittance (%) | | | Light transmittance after 1000 hrs (%) | | |
|---|---|---|---|---|---|---|---|
| | | 330 nm | 400 nm | 600 nm | 330 nm | 400 nm | 600 nm |
| 35 | Example 20 | 0 | 82 | 91 | 0 | 81 | 87 |
| 36 | Example 23 | 0 | 83 | 89 | 0 | 80 | 85 |
| 37 | Example 29 | 0 | 80 | 90 | 0 | 81 | 92 |
| 38 | Example 34 | 0 | 79 | 85 | 0 | 79 | 85 |

The fluorine-containing benzophenone derivatives of the present invention have polyfluorohydrocarbon groups in their molecules. Thus, they have superior heat resistance to conventional ultraviolet absorbers and can be incorporated to resins which require a high temperature for molding. Further, they are excellent in the weather resistance, and thus they are effective for a long period of time. Further, the fluorine-containing benzophenone derivatives of the present invention have excellent compatibility not only with usual resins but also with fluorine resins. Thus, they can be incorporated to fluorine resins to which it used to be difficult to incorporate conventional ultraviolet absorbers, without bringing about a whitening phenomenon, and they are capable of imparting ultraviolet absorptivity without impairing the transparency of the resins. Furthermore, when the fluorine-containing benzophenone derivatives of the present invention are incorporated to resins for filming, it is possible to obtain excellent transparent films. Such films are excellent materials capable of almost completely absorbing lights in the ultraviolet region, and they are excellent also in the weather resistance.

What is claimed is:

1. A fluorine-containing benzophenone derivative of the formula (1), (2) or (3):

   (1)

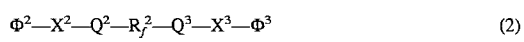   (2)

   (3)

wherein $\Phi^1$ is a 2-hydroxybenzophenone structure of the formula ka-1:

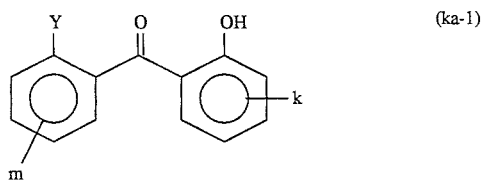

(wherein Y is a hydrogen atom or a hydroxyl group, each of k and m indicates the number of bond sites, k is an integer of from 0 to 3, and m is an integer of from 0 to 3, provided that $1 \leq (k+m) \leq 4$), n corresponds to (k+m) and is an integer of from 1 to 4, each of $\Phi^2$, $\Phi^3$, $\Phi^4$, and $\Phi^5$ is a 2-hydroxybenzophenone structure of the formula ka-1 wherein (k+m) is 1, each of $X^1$, $X^2$, $X^3$, $X^4$ and $X^5$ is a single bond or an oxygen atom, $Q^1$ is a single bond or a bivalent linking group having a carbon atom directly bonded to $X^1$, each of $Q^2$ and $Q^3$ is a single bond or a bivalent linking group, $R_f^1$ is a monovalent polyfluorohydrocarbon group having from 2 to 22 carbon atoms, in which some of the carbon atoms may be substituted by ether oxygen atoms, $F_f^2$ is a bivalent polyfluorohydrocarbon group having from 2 to 22 carbon atoms, in which some of the carbon atoms may be substituted by ether oxygen atoms, and $Q_f$ is a bivalent linking group having at least one $Q^4$—$R_f^1$ (wherein $Q^4$ is a bivalent linking group, and $R_f1$ is as defined above), wherein said bivalent linking group is —$(CH_2)_p$—, —$(CH_2)_g$—CH(OR$^1$)—$(CH_2)_q$—, —$(CH_2)_a$— COO—(CH$_2)_b$—, —$(CH_2)_c$—COO—$(CH_2)_f$—N(R$^3$)SO$_2$— or —$(CH_2)_e$—OCO—$(CH_2)_f$—N(R$^4$)SO$_2$— (wherein p is an integer of from 2 to 8, g is an integer of from 0 to 8, q is an integer of from 1 to 8, each of a and c is an integer of from 0 to 6, each of b, d, g and f is an integer of from 1 to 8, R$^1$ is a hydrogen atom or an acyl group, and each of R$^3$ and R$^4$ is an alkyl group having from 1 to 3 carbon atoms.

2. The fluorine-containing benzophenone derivative according to claim 1, wherein in the formula (1), $R_f^1$ is a monovalent polyfluorohydrocarbon group having from 6 to 14 carbon atoms, $X^1$ is an oxygen atom, n is 1, $Q^1$ is —$(CH_2)_p$—, —$(CH_2)_g$—CH(OR$^1$)—$(CH_2)_q$—, —$(CH_2)_a$—COO—$(CH_2)_b$—, —$(CH_2)_c$—COO—$(CH_2)_d$—N(R$^3$)SO$_2$— or —$(CH_2)_e$—OCO—$(CH_2)_f$—N(R$^4$)SO$_2$— (wherein p is an integer of from 2 to 8, g is an integer of from 0 to 8, q is an integer of from 1 to 8, each of a and c is an integer of from 0 to 6, each of b, d, g and f is an integer of from 1 to 8, R$^1$ is a hydrogen atom or an acyl group, and each of R$^3$ and R$^4$ is an alkyl group having from 1 to 3 carbon atoms).

3. The fluorine-containing benzophenone derivative according to claim 1, wherein in the formula (1), $R_f^1$ is a monovalent polyfluorohydrocarbon group having from 6 to 14 carbon atoms, $X^1$ is an oxygen atom, n is 1, $Q^1$ is —$(CH_2)_g$—CH(OR$^1$)—$(CH_2)_q$— or —$(CH_2)_a$—COO—$(CH_2)_b$— (wherein g is an integer of from 0 to 8, q is an integer of from 1 to 8, a is an integer of from 0 to 6, b is an integer of from 1 to 8, and R$^1$ is a hydrogen atom).

4. The fluorine-containing benzophenone derivative according to claim 1, wherein in the formula (1), $R_f^1$ is a monovalent polyfluorohydrocarbon group having from 6 to 14 carbon atoms having a carbon-carbon unsaturated double bond, $X^1$ is an oxygen atom, n is 1, and $Q^1$ is a single bond.

5. The fluorine-containing benzophenone derivative according to claim 1, wherein in the formula (3), each of $X^4$ and $X^5$ is an oxygen atom, $Q_f$ is a bivalent linking group of the formula (4):

wherein each of $Q^4$, $Q^5$ and $Q^6$ is a bivalent linking group, and $R_f^1$ is a monovalent polyfluorohydrocarbon group having from 2 to 22 carbon atoms, in which some of the carbon atoms may be substituted by ether oxygen atoms.

6. The fluorine-containing benzophenone derivative according to claim 5, wherein in the formula (4), $Q^4$ is a bivalent linking group, $R_f^1$ is a monovalent polyfluorohydrocarbon group having from 2 to 22 carbon atom, in which some of the carbon atoms may be substituted by ether oxygen atoms, and each of $Q^5$ and $Q^6$ is —$(CH_2)_p$—, —$(CH_2)_g$—CH(OR$^1$)—$(CH_2)_q$— or —$(CH_2)_a$—COO—$(CH_2)_b$— (wherein p is 1, g is an integer of 0 or 1, q is an integer of 1 or 2, a is an integer of 0 or 1, b is an integer of from 1 to 6, and R$^1$ is a hydrogen atom).

7. An ultraviolet absorber comprising a fluorine-containing benzophenone derivative as defined in claim 1.

8. The fluorine-containing benzophenone derivative according to claim 1, of the formula
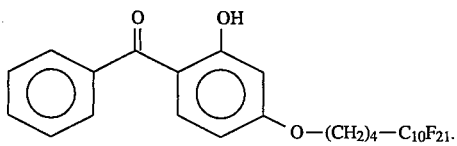
9. The fluorine-containing benzophenone derivative according to claim 1, of the formula
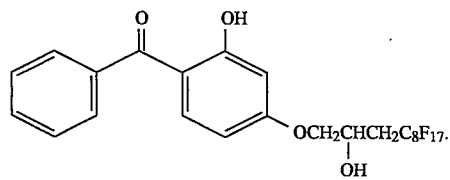
10. The fluorine-containing benzophenone derivative according to claim 1, of the formula
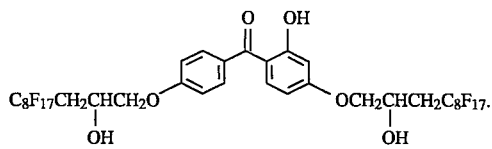
* * * * *